United States Patent
Waisman et al.

(10) Patent No.: US 11,446,087 B2
(45) Date of Patent: Sep. 20, 2022

(54) MEDICAL OPTICAL FIBER WITH PROTECTIVE TIP AND METHOD OF MANUFACTURE THEREFOR

(71) Applicant: LUMENIS LTD., Yokneam (IL)

(72) Inventors: Tal Waisman, Haifa (IL); Arkady Khachaturov, Haifa (IL)

(73) Assignee: Lumenis Ltd., Yokneam (IL)

( * ) Notice: Subject to any disclaimer, the term of this patent is extended or adjusted under 35 U.S.C. 154(b) by 546 days.

(21) Appl. No.: 16/388,697

(22) Filed: Apr. 18, 2019

(65) Prior Publication Data

US 2019/0314086 A1    Oct. 17, 2019

Related U.S. Application Data

(63) Continuation-in-part of application No. 15/954,443, filed on Apr. 16, 2018, now abandoned.

(60) Provisional application No. 62/661,023, filed on Apr. 22, 2018.

(51) Int. Cl.
*A61B 18/22* (2006.01)
*G02B 6/44* (2006.01)

(52) U.S. Cl.
CPC .............. *A61B 18/22* (2013.01); *G02B 6/443* (2013.01); *G02B 6/4486* (2013.01); *A61B 2018/2222* (2013.01); *A61B 2018/2244* (2013.01)

(58) Field of Classification Search
CPC combination set(s) only.
See application file for complete search history.

(56) References Cited

U.S. PATENT DOCUMENTS

| | | | |
|---|---|---|---|
| 9,031,370 B2 | 5/2015 | Khachaturov | |
| 9,067,059 B2* | 6/2015 | Bissig | A61N 5/0624 |
| 9,968,404 B2 | 5/2018 | Ashraf et al. | |
| 2009/0240242 A1 | 9/2009 | Neuberger | |
| 2009/0287198 A1* | 11/2009 | Hanley | G02B 6/262 |
| | | | 606/15 |
| 2010/0016845 A1* | 1/2010 | Hanley | A61B 18/24 |
| | | | 606/15 |
| 2017/0079716 A1* | 3/2017 | Zerfas | A61B 18/22 |
| 2019/0083177 A1* | 3/2019 | Brown | G02B 6/443 |

FOREIGN PATENT DOCUMENTS

WO    2017192869 A1    11/2017

OTHER PUBLICATIONS

Search Report—Corresponding PCT Application No. PCT/IL2019/050453, dated Aug. 15, 2019, 5 pages.
Extended European Search Report of EP Application No. 19792033.3, dated Dec. 20, 2021, 6 pages.

* cited by examiner

*Primary Examiner* — Scott Luan
(74) *Attorney, Agent, or Firm* — Seager, Tufte & Wickhem, LLP

(57) ABSTRACT

The present invention is directed towards medical optical fibers with protective tips for use with endoscopes for laser based treatment of internal bodily organs and method of manufacture therefor. The medical optical fibers have a short stripped medical optical fiber section and a protective tip provided thereon to encapsulate both the stripped medical optical fiber section and the jacket tip immediately therebehind.

16 Claims, 3 Drawing Sheets

US 11,446,087 B2

MEDICAL OPTICAL FIBER WITH PROTECTIVE TIP AND METHOD OF MANUFACTURE THEREFOR

RELATED APPLICATION

This application is related to and claims priority to U.S. provisional patent application Ser. No. 62/661,023 filed Apr. 22, 2018, and is a Continuation-In-Part of U.S. patent application Ser. No. 15/954,443 filed Apr. 16, 2018, the entire contents of each of which are herein incorporated by reference. This application is also related to U.S. Pat. No. 9,031,370, the entire contents of which are herein incorporated by reference.

FIELD OF THE INVENTION

The present invention relates to medical optical fibers for use with endoscopes for laser based treatment of internal bodily organs and a method of manufacture therefor.

BACKGROUND OF THE INVENTION

Medical optical fibers include a concentric arrangement of an optical fiber and a jacket surrounding the optical fiber. Optical fibers include an innermost optical core and at least one transparent cladding layer (hereinafter referred to as a "cladding layer") surrounding the optical core. The cladding layer necessarily has a lower refractive index than the optical core. Optical fibers optionally include at least one mechanical support layer (hereinafter referred to as a "mechanical support layer") surrounding a cladding layer. Medical optical fibers can have their jackets stripped similar to electrical wires to leave a stripped medical optical fiber section or a bare optical fiber section. Medical optical fiber diameters are in the range of a few ten microns to a few hundred microns and therefore a distal medical optical fiber tip tends to be sharp.

Optical energy which is produced by medical lasers is often delivered to a target tissue through a medical optical fiber. Targeting an internal bodily organ typically requires an endoscope. Passage of a medical optical fiber through an endoscope can be problematic even perforating same. In operation, depending on the laser energy being delivered, an optical fiber tip can erode faster than a jacket tip which leads to an optical fiber tip being recessed with respect to its jacket tip which is detrimental to continued operation. In liquid environments, optical fibers are subject to cavitation forces which lead to erosion. Different concentric layers of medical optical fibers are affected differently by cavitation forces.

Commonly owned U.S. Pat. No. 9,968,404 to Ashraf et al. is directed towards medical optical fibers having a smooth tip addition for assisting in passage of a medical optical fiber through an endoscope. U.S. Pat. No. 9,968,404 discloses the provision of a smooth tip addition on a distal medical optical fiber tip. Tip additions are designed to shatter, fragment, melt or otherwise be destroyed on firing laser pulses to expose an optical core. Tip additions can have a spherical shape surface, a hemi-spherical shaped surface, a curved shaped surface, and the like. Tip additions can be formed from a wide range of polymeric materials including inter alia epoxy materials, acrylate materials, UV-glues, and the like. Tip additions can be formed on an optical fiber tip by way of known manufacturing techniques including curing, gluing, and the like.

Commonly owned U.S. Pat. No. 9,031,370 to Khachaturov is directed towards medical optical fibers having a jacket which is grooved towards its jacket tip such that it flakes off in a controlled fashion rather than in a random fashion as a distal optical core end erodes.

There is a need for medical optical fibers with a tip for assisting in their passage through an endoscope to reach a target tissue in an internal bodily organ and also affording protection against cavitation forces in liquid environments.

SUMMARY OF THE INVENTION

In an aspect, a medical optical fiber for use with an endoscope for laser based treatment of internal bodily organs includes a longitudinal medical optical fiber axis; the medical optical fiber including: an optical fiber having a distal optical fiber tip, said optical fiber tip having an optical fiber end face transverse to the longitudinal medical optical fiber axis, said optical fiber including an innermost optical core having an optical core end face central at said optical fiber end face; a jacket surrounding said optical fiber, said jacket having a distal jacket tip with a jacket end face transverse to the longitudinal medical optical fiber axis, said jacket tip having a maximum external dimension D1 transverse to the longitudinal medical optical fiber axis, said jacket end face being recessed with respect to said optical fiber end face to leave a stripped medical optical fiber section; and a protective tip encapsulating said optical fiber end face and said jacket end face therewithin and having an external maximum dimension D2 transverse to the longitudinal medical optical fiber axis where D2>D1. The protective tip may have a leading protective tip surface forward of said optical fiber end face and a trailing protective tip surface spaced apart from said jacket end face along the longitudinal medical optical fiber axis, whereby said protective tip encapsulates said stripped medical optical fiber section and overlaps said jacket tip between said jacket end face and said trailing protective tip surface. The protective tip may be made of material which absorbs laser energy and one or more of fragments or melts, wherein on delivery of laser energy through the medical optical fiber, at least some of said leading protective tip surface forward of said optical fiber end face fragments or melts for enabling delivery of laser energy through said optical core end face to an internal bodily organ.

In another aspect, the jacket may be made from a polymeric material having a melting temperature T1 and the protective tip may be made from a polymeric material having a curing temperature T2 where T2<T1.

In yet another aspect, the stripped medical optical fiber section may have a length L of 350±150 μm measured from said optical fiber end face along the longitudinal medical optical fiber axis, and the stripped medical optical fiber section's peripheral surface may be treated for assisting provision of said protective tip.

In a further aspect, the jacket tip may be formed with at least one aperture for exposing an optical fiber layer underlying said jacket tip such that the protective tip contacts said underlying layer through said at least one aperture.

In yet a further aspect, an aperture of the at least one aperture may be co-directional with the longitudinal medical optical fiber axis. The aperture may extend from said jacket end face. Further, an aperture of the at least one aperture may be transverse to the longitudinal medical optical fiber axis.

In an aspect, a method of manufacturing a medical optical fiber for use with an endoscope for laser based treatment of internal bodily organs, includes the steps of: (a) providing a medical optical fiber having a longitudinal medical optical fiber axis, the medical optical fiber having an optical fiber having a distal optical fiber tip, the optical fiber tip having an optical fiber end face transverse to the longitudinal medical optical fiber axis; the optical fiber may include an innermost optical core having an optical core end face central at the optical fiber end face, and a jacket surrounding the optical fiber, the jacket having a distal jacket tip with a jacket end face transverse to the longitudinal medical optical fiber axis; the jacket tip may have an external maximum dimension D1 transverse to the longitudinal medical optical fiber axis; the jacket end face may be recessed with respect to the optical fiber end face to leave a stripped medical optical fiber section; and providing a protective tip encapsulating the optical fiber end face and the jacket end face therewithin and having an external maximum dimension D2 transverse to the longitudinal optical fiber axis where D2>D1; the protective tip having a leading protective tip surface forward of the optical fiber end face and a trailing protective tip surface spaced apart from the jacket end face along the longitudinal medical optical fiber axis whereby the protective tip encapsulates the stripped medical optical fiber section and overlaps the jacket tip between the jacket end face and the trailing protective tip surface; the protective tip being made of material which absorbs laser energy and one or more of fragments or melts, wherein on delivery of laser energy through the medical optical fiber, at least some of the leading protective tip surface forward of the optical fiber end face fragments or melts for enabling delivery of laser energy through the optical core end face to an internal bodily organ.

In another aspect, the jacket may be made from a polymeric material having a melting temperature T1 and the protective tip is made from a polymeric material having a curing temperature T2 where T2<T1.

In a further aspect, the stripped optical fiber core may have a length L of 150±50 μm measured from the optical fiber end face along the longitudinal optical fiber axis. Further, the stripped medical optical fiber section's peripheral surface may be treated for assisting provision of the protective tip.

In another aspect, the method further includes the step of forming the jacket tip with at least one aperture for exposing an optical fiber layer underlying the jacket tip such that the protective tip contacts the underlying layer through the at least one aperture. Also, it may include the step of forming an aperture co-directional with the longitudinal medical optical fiber axis and/or the step of forming an aperture extending from the jacket end face and/or the step of forming an aperture transverse to the longitudinal medical optical fiber axis.

The present invention is directed towards medical optical fibers with protective tips for use with endoscopes for laser based treatment of internal bodily organs and method of manufacture therefor. Protective tips of the present invention are similar to the above described tip additions in terms of assisting passage of medical optical fibers through an endoscope and being designed to shatter, fragment, melt or otherwise be destroyed on firing laser pulses to expose at least an optical core end face for enabling delivery of laser energy to an internal bodily organ. But in contradistinction to the above described tip additions, the medical optical fibers of the present invention have a short stripped medical optical fiber section and a protective tip provided thereon to encapsulate both the stripped medical optical fiber section and the jacket tip immediately therebehind. Accordingly, protective tips of the present invention overlap jacket material at a jacket tip. Moreover, the protective tips of the present invention protect a jacket tip from collapse of cavitation bubbles which in turn protects an optical fiber tip.

Thus, protective tips of the present invention afford smooth passage of medical optical fibers through an endoscope and protection of optical fiber tips during laser treatments.

Protective tips can be provided on medical optical fibers by employing conventional manufacturing techniques which do not militate against their construction or operation. Such conventional manufacturing techniques include inter alia gluing, curing, and the like. Some conventional manufacturing techniques require taking into consideration mechanical and chemical properties of the component layers of medical optical fibers. Medical optical fibers are preferably prepared to assist provisioning a protective tip thereon. One possible preparatory includes preparing a stripped medical optical fiber section such that it presents a roughened surface. Another possible preparatory step includes chemically and/or physically preparing a stripped medical optical fiber section's peripheral surface to present a surface with higher adhesion capabilities. As mentioned hereinabove, some medical optical fibers include a mechanical support layer immediately underlying a jacket. Some jacket materials, for example, Teflon, have a low adhesion capability. Accordingly, one or more throughgoing apertures can be formed in a jacket tip to expose a mechanical support layer or a cladding layer. Protective tips contact an exposed mechanical support layer or a cladding layer through the apertures for securing purposes. The apertures can be formed in a wide range of shapes and orientations.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF THE PRESENT INVENTION

Medical Optical Fibers with Protective Tip

Figure 1:
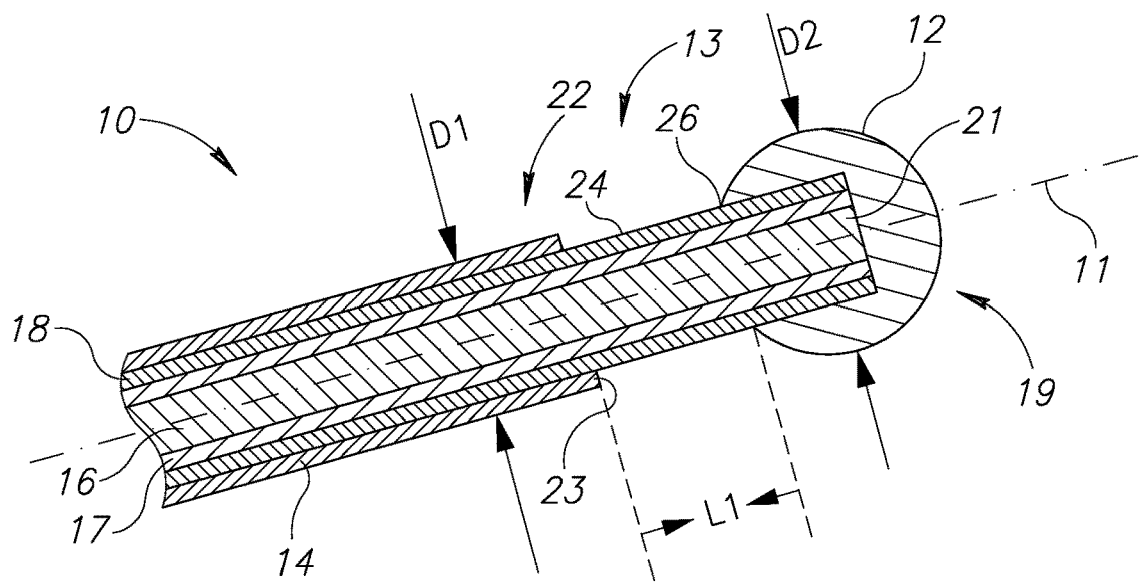
FIG. 1 is a longitudinal cross section of a medical optical fiber including a tip addition in accordance with commonly owned U.S. Pat. No. 9,968,404.

FIG. 1 shows a medical optical fiber 10 having a longitudinal medical optical fiber axis 11 and a tip addition 12 in accordance with commonly owned U.S. Pat. No. 9,968,404. The medical optical fiber 10 includes a concentric arrangement of an optical fiber 13 and a jacket 14 surrounding the optical fiber 13. The optical fiber 13 includes an innermost optical core 16, a cladding layer 17 surrounding the optical core 16 and a mechanical support layer 18 surrounding the cladding layer 17. The optical fiber 13 has a distal optical fiber tip 19 with an optical fiber end face 21 transverse to the longitudinal medical optical fiber axis 11. The jacket 14 has a distal jacket tip 22 with a jacket end face 23 transverse to the longitudinal medical optical fiber axis 11.

The medical optical fiber 10 has a stripped medical optical fiber section 24 from a tip addition's trailing surface 26 to the jacket end face 23. The stripped medical optical fiber section 24 has a length L1 in the region of 50-2,000 micron along the longitudinal medical optical fiber axis 11. The jacket 14 has an external maximum dimension D1. The tip addition 12 is cured on the optical fiber tip 19 and encapsulates the optical fiber end face 21 therewithin. The tip addition 12 has an external maximum dimension D2 transverse to the longitudinal medical optical fiber axis 11 where D2>D1. The tip addition's D2 is smaller than a working channel of an endoscope's internal diameter for passage therethrough.

Figure 2:
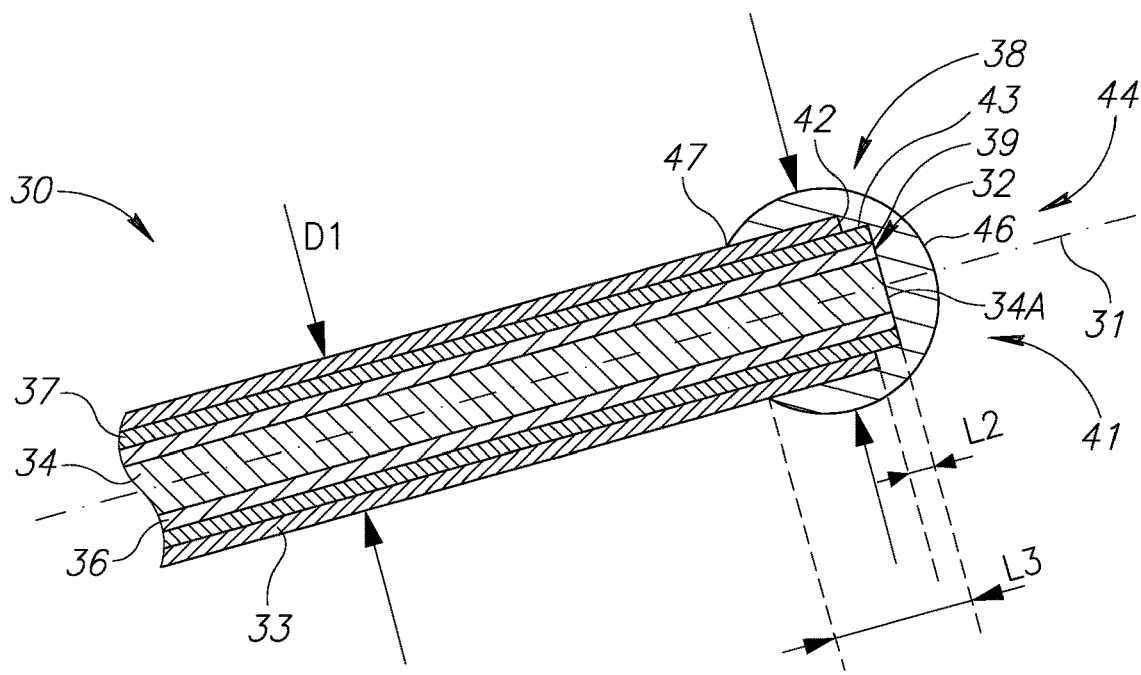
FIG. 2 is a longitudinal cross section of a medical optical fiber including a protective tip in accordance with a first embodiment of the present invention.

FIG. 2 shows a medical optical fiber 30 has a longitudinal medical optical fiber axis 31 and includes a concentric arrangement of an optical fiber 32 and a jacket 33 surrounding the optical fiber 32. The optical fiber 32 includes an innermost optical core 34, a cladding layer 36 surrounding the optical core 34 and a mechanical support layer 37 surrounding the cladding layer 36. The optical fiber 32 has a distal optical fiber tip 38 with an optical fiber end face 39 transverse to the longitudinal medical optical fiber axis 31. The optical core 34 has an optical core end face 34A centered at the optical fiber end face 39. The jacket 33 has a jacket tip 41 with a jacket end face 42 transverse to the longitudinal medical optical fiber axis 31. The jacket 33 has an external maximum dimension D1. The medical optical fiber 30 has a stripped medical optical fiber section 43 from the optical fiber end face 39 to the jacket end face 42. The stripped medical optical fiber section 43 has a length L2 in the region of 350±150 µm measured from the optical fiber end face 39 along the longitudinal medical optical fiber axis 31.

The medical optical fiber 30 has a protective tip 44 mounted on the optical fiber tip 38 to encapsulate the optical fiber end face 39 and the jacket end face 42. The protective tip 44 has a leading protective tip surface 46 forward of the optical fiber end face 39. The protective tip 44 has a trailing protective tip surface 47 longitudinally spaced apart from the jacket end face 42 by a length L3 in the region of 800±300 µm measured from the optical fiber end face 39 along the longitudinal medical optical fiber axis 31. Accordingly, the protective tip 44 encapsulates the stripped medical optical fiber section 43 and overlaps the jacket tip 41 between the jacket end face 42 and the trailing protective tip surface 47. The protective tip 44 has an external maximum dimension D2 transverse to the longitudinal medical optical fiber axis 31 where D2>D1.

The protective tip 44 can be made from a wide range of polymeric materials which may be cured. Curing can be way of temperature curing, chemical curing, radiation curing, and the like. Radiation curing can include IR curing, UV curing, visible light curing, and the like. Suitable protective tip materials include inter alia epoxy, acrylate, and the like. Different materials can be used for different jacket/protective tip combinations depending on a selected manufacturing technique. A necessary condition in the case of temperature curing is that a jacket's polymeric material has a melting temperature T1 and a protective tip's polymeric material has a curing temperature T2 where T2<T1 to avoid melting a jacket. Preferably T2/T1>1.1. Depending on a polymeric material employed for a protective tip, temperature curing of a protective tip can take place at room temperature.

In use, delivery of laser energy through a medical optical fiber 30 causes at least some of the leading protective tip surface 46 forward of the optical fiber end face 39 to fragment or melt for enabling delivery of laser energy through the optical core end face 34A to an internal bodily organ.

Figure 3:
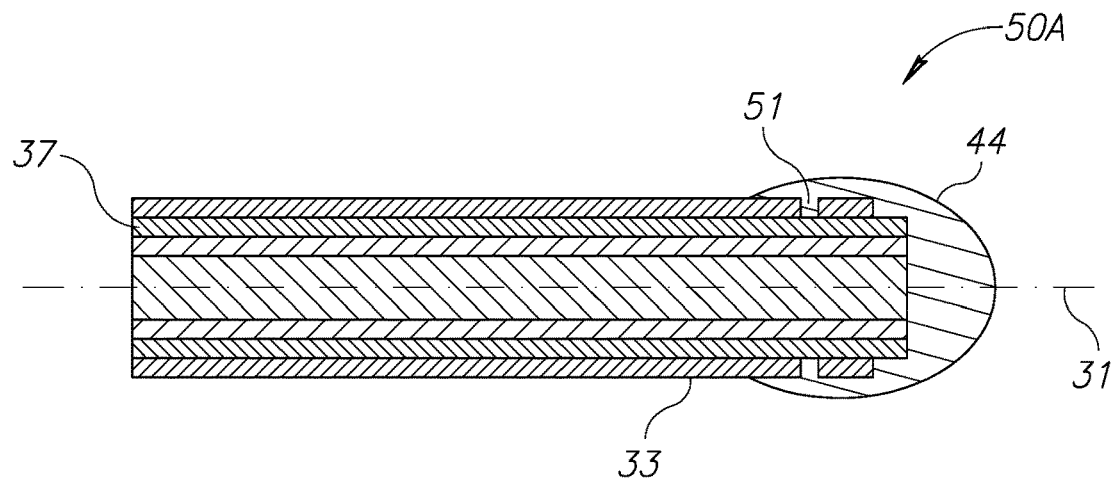
FIG. 3 is a longitudinal cross section of a medical optical fiber including a grooved distal jacket tip and a protective tip in accordance with a second embodiment of the present invention.

FIG. 3 shows a medical optical fiber 50A similar to the medical optical fiber 30 and therefore similar parts are likewise numbered. The medical optical fiber 50 differs from the medical optical fiber 30 insofar as the jacket 33 is formed with at least one aperture constituted by one or more grooves 51 transverse to the longitudinal medical optical fiber axis 31 to expose the mechanical support layer 37 therethrough. Accordingly mounting of the protective tip 44 on the optical fiber 50A leads to protective tip material contacting the mechanical support layer 37 or cladding layer 36 through grooves 51. Contact of protective tip material on the mechanical support layer 37 has greater adhesive strength than contact on the jacket 33. Grooves 51 can be made even deeper such that they expose the cladding layer 36.

Figure 4:
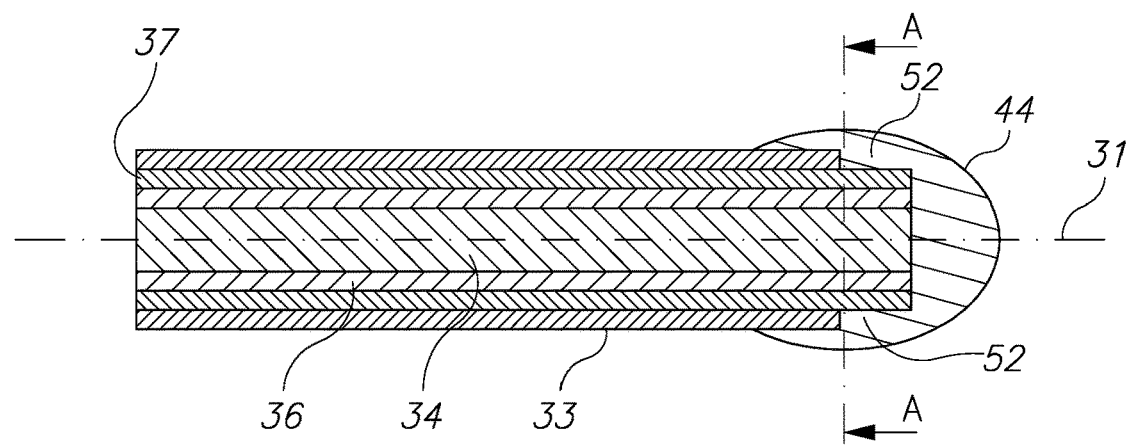
FIG. 4 is a longitudinal cross section of a medical optical fiber including a grooved jacket tip and a protective tip in accordance with a third embodiment of the present invention.
Figure 5:
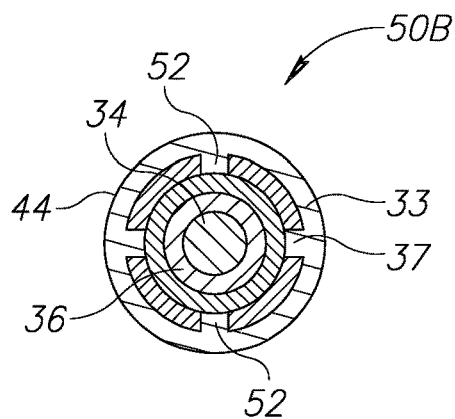
FIG. 5 is a transverse cross section of the FIG. 4 medical optical fiber along a line A-A in FIG. 4.
Figure 6A:
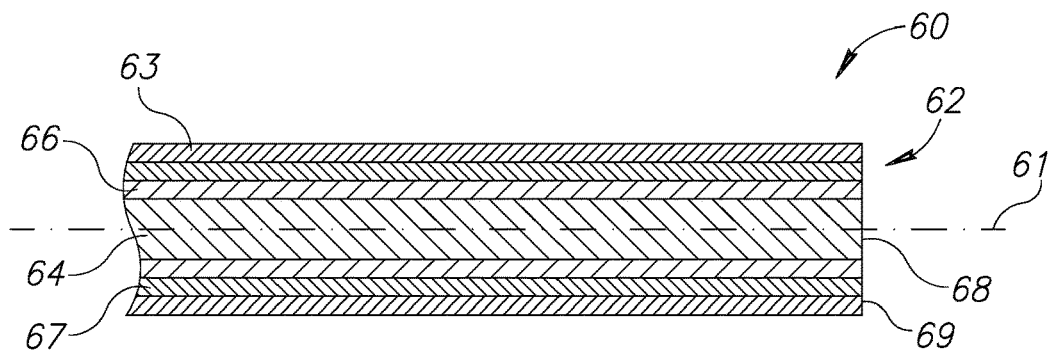
FIG. 6A to FIG. 6D show a method of manufacturing a medical optical fiber with a protective tip in accordance with the present invention.
Figure 6B:
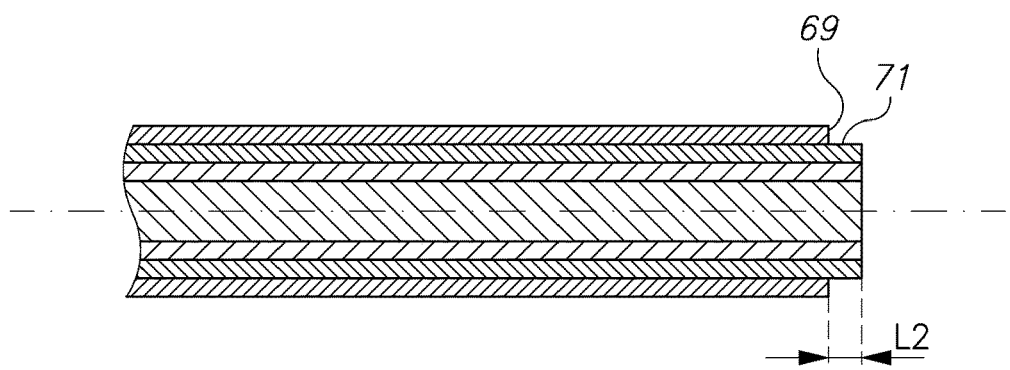
Figure 6C:
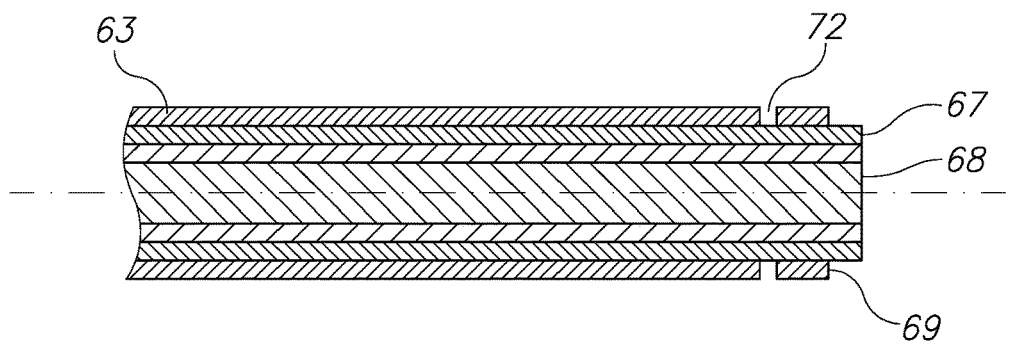
Figure 6D:
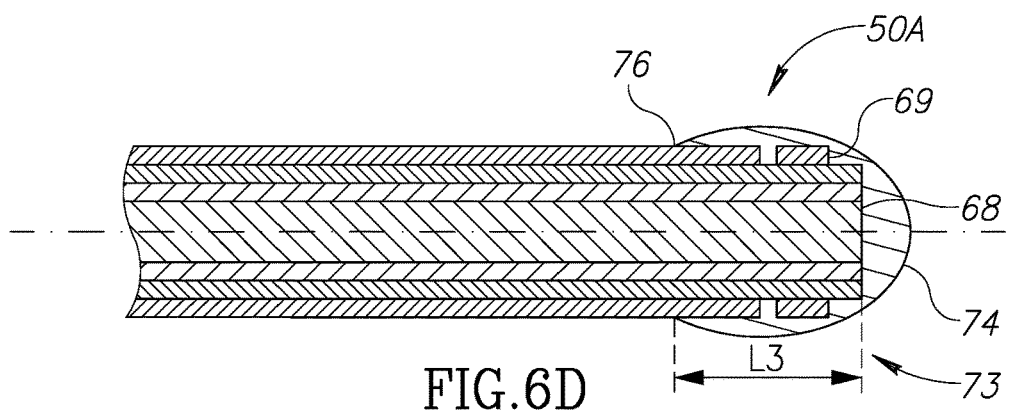

FIG. 4 and FIG. 5 show a medical optical fiber 50B similar to the medical optical fiber 50A but differing therefrom in terms its apertures for exposing the cladding layer 36 or the mechanical support layer 37. The medical optical fiber 50B includes grooves 52 co-directional with the longitudinal medical optical fiber axis 31. Grooves 52 can optionally extend from the jacket end face 42.

Method of Manufacture of Medical Optical Fiber with Protective Tip

The method of manufacturing a medical optical fiber 50A is now described with reference to FIG. 6A to FIG. 6D and includes the following steps:

Step 1: Provide a standard medical optical fiber 60 having a longitudinal medical optical fiber axis 61. The medical optical fiber 60 includes a concentric arrangement of an optical fiber 62 and a jacket 63 surrounding the optical fiber 62. The optical fiber 62 includes an innermost optical core 64, a cladding layer 66 surrounding the optical core 64 and a mechanical support layer 67 surrounding the cladding layer 66. The optical fiber 62 has an optical fiber end face 68. The jacket 63 has a jacket end face 69 flush with the optical fiber end face 68.

Step 2: Strip the medical optical fiber 60 to form a stripped medical optical fiber section 71. The stripped medical optical fiber section 71 has a length L2 in the region of 350±150 µm measured from the optical fiber end face 68 along the longitudinal medical optical fiber axis 61.

Step 3: Form grooves 72 in the jacket 63 towards the jacket end face 69 to expose the mechanical support layer 67. The grooves can be possibly deepened to expose the cladding layer 66.

Step 4: Treat stripped medical optical fiber section 71's peripheral surface to improve adhesion by a protective tip 73.

Step 5: Provide a protective tip 73 on the medical optical fiber 60 to encapsulate the optical fiber end face 68 and the jacket end face 69. The protective tip 73 has a leading protective tip surface 74 forward of the optical fiber end face 68. The protective tip 73 has a trailing protective tip surface 76 spaced apart from the jacket end face 69 along the longitudinal medical optical fiber axis 61 by a length L3 measured from the optical fiber end face 68 where L3 in the region of 450±50 µm.

While the invention has been described with respect to a limited number of embodiments, it will be appreciated that many variations, modifications, and other applications of the invention can be made within the scope of the appended claims.

The invention claimed is:

1. A medical optical fiber for use with an endoscope for laser based treatment of internal bodily organs, the medical optical fiber comprising:
   an optical fiber having a distal optical fiber tip, said distal optical fiber tip having an optical fiber end face transverse to a longitudinal axis of the medical optical fiber, the optical fiber including an innermost optical core having an optical core;
   a jacket surrounding said optical fiber, said jacket having a distal jacket tip with a jacket end face transverse to the longitudinal axis, said jacket tip having a maximum external dimension D1, said jacket end face comprising a recessed portion at a distal end of the optical fiber proximal to the distal optical fiber tip, said recessed portion comprising a length L1, wherein L1 is greater than or equal to 200 micrometers (μm) and less than or equal to 500 μm; and
   a protective tip encapsulating said optical fiber end face and said jacket end face therewithin and having an external maximum dimension D2 transverse to the longitudinal axis, wherein D2 is greater than or equal to D1,
   said protective tip having a leading protective tip surface forward of said optical fiber end face and a trailing protective tip surface spaced apart from said jacket end face along the longitudinal axis whereby said protective tip encapsulates said optical fiber end face and said recessed portion overlaps said jacket tip between said jacket end face and said trailing protective tip surface, wherein said trailing protective tip comprises a length extending proximally from said optical fiber end face of greater than or equal to 400 μm and less than or equal to 1100 μm, and
   said protective tip being made of material which fragments or melts on incidence of laser energy to enable delivery of laser energy through said optical core end face to an internal bodily organ.

2. The fiber according to claim 1 wherein said jacket is made from a polymeric material having a melting temperature T1 and said protective tip is made from a polymeric material having a curing temperature T2 where T2<T1.

3. The fiber according to claim 1 wherein the recessed portion exposes a stripped medical optical fiber section, said stripped medical optical fiber section's peripheral surface is treated for assisting provision of said protective tip.

4. The fiber according to claim 1 wherein said jacket tip is formed with at least one aperture for exposing an optical fiber layer underlying said jacket tip such that said protective tip contacts said underlying layer through said at least one aperture.

5. The fiber according to claim 4 wherein an aperture of said at least one aperture is co-directional with the longitudinal medical optical fiber axis.

6. The fiber according to claim 5 wherein said aperture extends from said jacket end face.

7. The fiber according to claim 4 wherein an aperture of said at least one aperture is transverse to the longitudinal medical optical fiber axis.

8. The fiber according to claim 1, wherein the optical core end face is a first length from the jacket end face, the jacket end face is a second length from a proximal end of the trailing protective tip surface, and the first length is less than the second length.

9. A method of manufacturing a medical optical fiber for use with an endoscope for laser based treatment of internal bodily organs, the method comprising:
   providing a medical optical fiber having a longitudinal axis, the medical optical fiber comprising:
      an optical fiber end face and an innermost optical core having an optical core end face at the optical fiber end face, and
      a jacket surrounding the optical fiber, the jacket having a distal jacket tip with a jacket end face transverse to the longitudinal axis, the distal jacket tip having an external maximum dimension D1, the jacket end face comprising a recessed portion at a distal end of the optical fiber proximal to the optical fiber the distal optical fiber tip, the recessed portion comprising a length L1, wherein L1 is greater than or equal to 200 micrometers (μm) and less than or equal to 500 μm; and
   providing a protective tip encapsulating the optical fiber end face, the jacket end face, and the recessed portion therewithin and having an external maximum dimension D2 transverse to the longitudinal axis, wherein D2 is greater than or equal to D1,
   the protective tip having a leading protective tip surface forward of the optical fiber end face and a trailing protective tip surface spaced apart from the jacket end face along the longitudinal medical optical fiber axis, wherein the trailing protective tip comprises a length extending proximally from said optical fiber end face of greater than or equal to 400 μm and less than or equal to 1100 μm, and
   the protective tip being made of material which fragments or melts on incidence of laser energy to enable delivery of laser energy through the optical core end face to an internal bodily organ.

10. The method according to claim 9 wherein the jacket is made from a polymeric material having a melting temperature T1 and the protective tip is made from a polymeric material having a curing temperature T2 where T2<T1.

11. The method according to claim 9 the recessed portion exposes a stripped medical optical fiber section, wherein the stripped medical optical fiber section's peripheral surface is treated for assisting provision of the protective tip.

12. The method according to claim 9 and further comprising forming the jacket tip with at least one aperture for exposing an optical fiber layer underlying the jacket tip such that the protective tip contacts the underlying layer through the at least one aperture.

13. The method according to claim 12 wherein step (c) includes forming an aperture co-directional with the longitudinal medical optical fiber axis.

14. The method according to claim 13 wherein step (c) includes forming an aperture extending from the jacket end face.

15. The method according to claim 12 wherein step (c) includes forming an aperture transverse to the longitudinal medical optical fiber axis.

16. The method according to claim 9, wherein the optical core end face is a first length from the jacket end face, the jacket end face is a second length from a proximal end of the trailing protective tip surface, and the first length is less than the second length.

* * * * *